United States Patent [19]

Mächler et al.

[11] Patent Number: 4,643,570

[45] Date of Patent: Feb. 17, 1987

[54] THROUGH-FLOW CUVETTE

[75] Inventors: Meinrad Mächler, Ellwangen; Richard Sachse, Königsbronn; Harry Schlemmer, Aalen, all of Fed. Rep. of Germany

[73] Assignee: Carl-Zeiss-Stiftung, Heidenheim, Fed. Rep. of Germany

[21] Appl. No.: 722,113

[22] Filed: Apr. 11, 1985

[30] Foreign Application Priority Data

Apr. 14, 1984 [DE] Fed. Rep. of Germany ....... 3414260

[51] Int. Cl.⁴ .............................................. G01N 1/10
[52] U.S. Cl. .................................... 356/246; 250/576
[58] Field of Search ................ 356/246, 244; 250/576, 250/573; 422/81

[56] References Cited

FOREIGN PATENT DOCUMENTS 2246225 4/1973 Fed. Rep. of Germany ...... 356/246

Primary Examiner—Eugene R. LaRoche
Assistant Examiner—Robert J. Pascal
Attorney, Agent, or Firm—Walter Ottesen

[57] ABSTRACT

The invention is directed to a through-flow cuvette which can be assembled and wherein the cuvette body is made of two cuvette halves. The cuvette halves are placed one atop the other at their planar surfaces. Convex recesses are formed in these planar surfaces and define the inlet and outlet channels as well as the measuring space.

17 Claims, 8 Drawing Figures

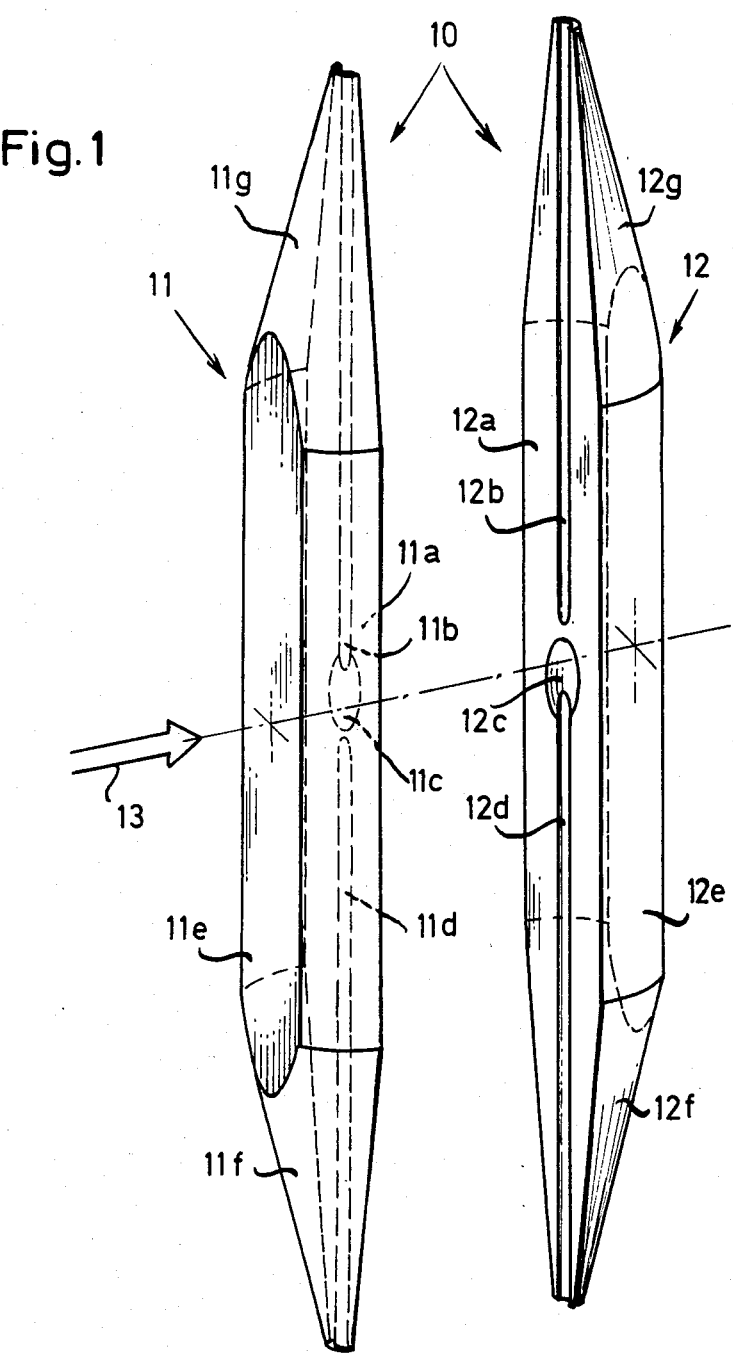

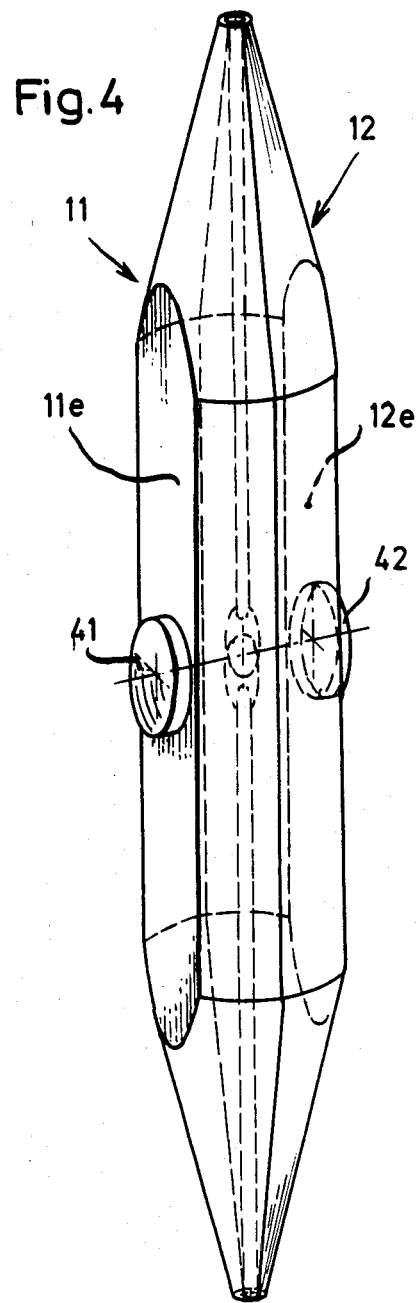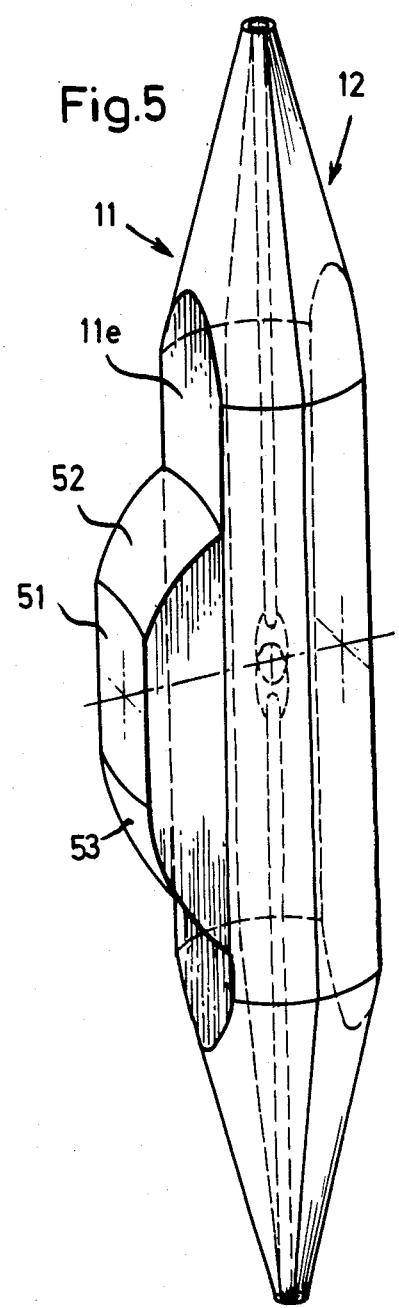

THROUGH-FLOW CUVETTE

FIELD OF THE INVENTION

The invention relates to a through-flow cuvette which can be assembled. The invention relates especially to a through-flow cuvette having the smallest possible volume, that is, with a measurement volume of only a few nanoliters. Cuvettes of this kind are especially advantageous in the area of micro high-pressure liquid chromatography.

BACKGROUND OF THE INVENTION

The small volumes associated with micro high-pressure liquid chromatography require a layer thickness in the range of a few to approximately 100 µm for a measuring beam having a cross section of one to a few mm². Cuvettes with a layer thickness of this kind are known from the infrared analysis techniques with respect to liquids. Generally, these cuvettes have two windows made of parallel plates separated from each other by a spacer of a corresponding thickness. The arrangement is seated in a housing which in most instances is of cylindrical configuration. The housing has an inlet and an outlet for the liquid. Cuvettes of this kind are described in German Pat. No. 16 48 917 and in U.S. Pat. No. 3,090,861. These cuvettes have the disadvantage that they are somewhat difficult to manipulate and are difficult to reproduce because of the relatively thin spacer. Furthermore, it is difficult to make these cuvettes seal-tight for the pressures of 100 to 1,000 bar that are used in high-pressure liquid chromatography.

German Pat. No. 21 58 220 discloses a through-flow cuvette assembled with at least three parallel plates. The center plate has a cutout which defines the measuring space and the inlet and outlet of the cuvette. However, this cuvette is not suitable for a very small measuring volume, that is, for a very small layer thickness because then the center plate would have to be so thin that it cannot be produced or manipulated.

SUMMARY OF THE INVENTION

In view of the above, it is an object of the invention to provide a cuvette which has a very small measuring volume. It is another object of the invention to provide a cuvette of this kind wherein the layer thickness is small and the cuvette is seal-tight at high pressures as well as being easy to manipulate.

The through-flow cuvette according to the invention includes two cuvette body halves of which at least one body half is made of an optically transparent material. The cuvette body halves have respective planar surfaces defining the interface between the body halves when the cuvette is assembled. Recess means are formed in the planar surfaces to define a measuring space as well as inlet and outlet channels communicating with the space.

According to another feature of the invention, the measuring space of the assembled cuvette is conjointly defined by two convex recesses formed in respective ones of the planar surfaces. The convex recesses are displaced with respect to each other in the direction of the channels. In this way, the layer thickness in the region provided for the measuring beam is approximately constant and an optical effect occurs in the measuring space which can be generally neglected.

According to another feature of the invention, both body halves of a cuvette can be dimensioned so that they have the same identical geometric dimensions and one of the body halves can be rotated 180° when placed atop the other one of the body halves. In a further embodiment of the invention, the convex recesses are configured so as to be spherical.

Both body halves can be configured so that they conjointly define a spindle-shaped cuvette. The spindle-shaped cuvette can be conically configured at the outer ends of the inlet and outlet channels.

At least one of the two body halves is made of an optically transmittable material such as glass, quartz or sapphire. When the cuvette is utilized in optical apparatus wherein the reflected light is measured, then the second cuvette body half is made of an optically opaque material. In this instance, the material should be one which has a good heat conductivity for the situation wherein the specimen is to be temperature controlled.

BRIEF DESCRIPTION OF THE DRAWING

The invention will now be described with reference to the drawing wherein:

FIG. 1 is a perspective view of the cuvette according to the invention shown disassembled;

FIG. 2b is a section view taken along line IIb–IIb of FIG. 2a;

FIG. 4 is another embodiment of the cuvette of the invention configured as an optical resonator for absorption measurements; and, FIG. 5 is a configuration of the cuvette of the invention as an optical resonator for reflection measurements.

DESCRIPTION OF THE PREFERRED EMBODIMENTS OF THE INVENTION

Figure 2B:
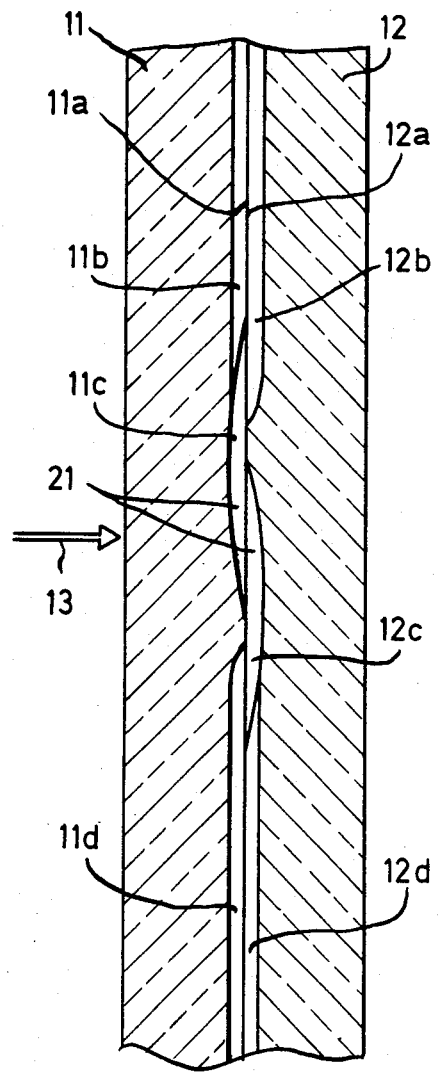

In FIG. 1, reference numeral 10 identifies a cuvette comprising two cuvette halves 11 and 12 which are shown spaced from each other to facilitate a clear showing thereof. The inlet channels 11b, 12b and convex recesses 11c, 12c are formed in the planar surfaces 11a, 12a of cuvette halves 11 and 12, respectively. The liquid or gas flows through these channels and recesses in the assembled condition of the cuvette. The planar surfaces 11a and 12a have optical surface qualities so that the cuvette body 10 in its assembled condition is seal-tight with respect to liquids at high pressure and gastight at normal pressure.

The cuvette halves have plane outer surfaces 11e and 12e which are parallel to the planar surfaces 11a and 12a, respectively. In the assembled condition, the cuvette halves form a cuvette body 10 having a spindle-like shape. At respective outer ends of the channels 11b, 12b and 11d, 12d, the cuvette body 10 has the shape of respective cones (11f, 12f) and (11g, 12g) for connecting to the inflow and outflow lines.

Figure 2A:
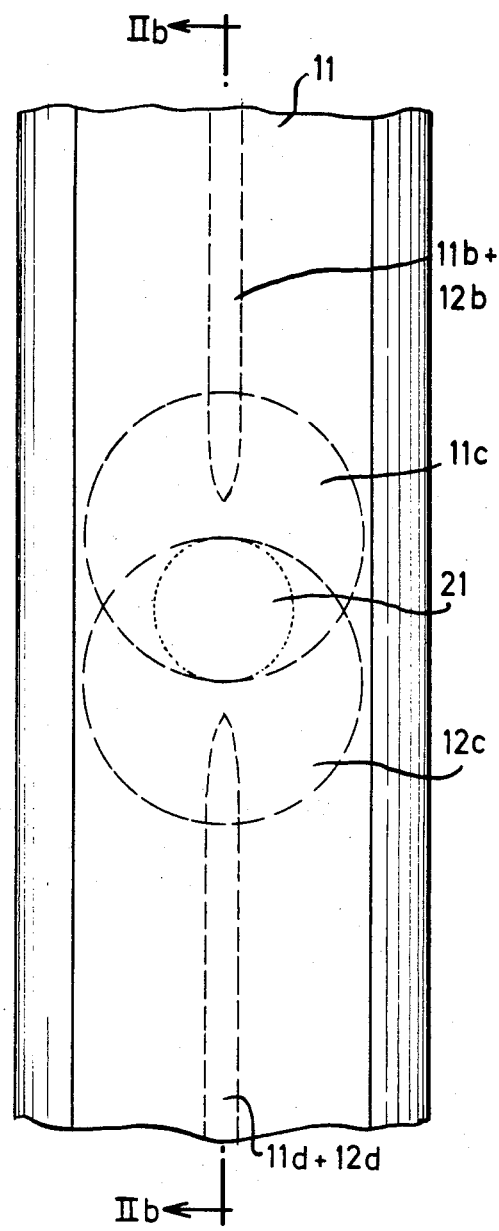
FIG. 2a is a plan view of a portion of the cuvette body viewed in the direction of the incident light beam.

FIG. 2a shows a portion of the cuvette body 10 viewed in the incidence direction 13 of the measuring beam. FIGS. 2a and 2b show that the convex recesses 11c and 12c are displaced with respect to each other in the direction of the channels 11b, 12b, 11d and 12d so that the cross section 21 provided for the measuring beam has an approximately constant layer thickness. If spherical surfaces are used for the convex recesses 11c and 12c having center points displaced by an amount equal to half of the diameter of the recesses, there results a cuvette having dimensions to be provided below, a focal width between −0.5 and −1.0 m according to the refractive index of the specimen by means of the nonparallel boundary surfaces in the cross section 21. An optical effect of this kind has no significant disturbing influence in most applications.

The cuvette body 10 described above can be made with the following dimensions: total length=25 mm; diameter=8 mm; distance between planar surfaces 11e and 12e=6 mm; radius of the spherical recesses=500 to 1,000 mm; center depth of the spherical recesses=3 to 10 μm; diameter of the cross section 21 for the measuring beam=1 to 3 mm; diameter of the channels=0.1 to 0.5 mm. Preferably, the dimensions of the channels and the dimensions of the convex recesses are selected with respect to each other so that the flow cross section remains approximately constant.

Figure 3A:
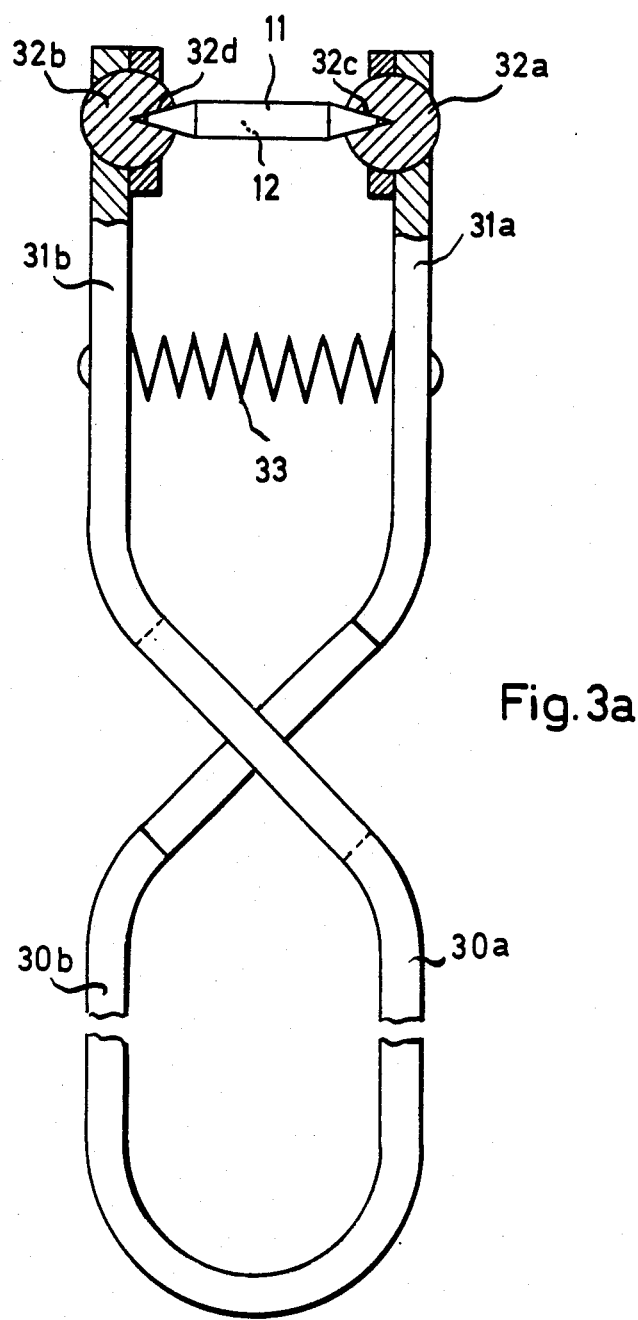
FIG. 3a is a device for precisely placing the two halves of the cuvette one atop the other.

To ensure a trouble free operation of the cuvette, it is necessary that the cuvette halves 11 and 12 are placed exactly one atop the other. For this purpose, the device shown in FIG. 3a is utilized and is in the form of adjusting tongs. The ends 31a and 31b move apart by the application of pressure on the locations 30a and 30b thereof. Rotatably mounted spheres 32a and 32b are mounted at respective ends 31a and 31b of the device. The spheres 32a and 32b can be made of Teflon and can be provided with conical recesses 32c and 32d. The angle of the conical recesses correspond precisely to the cones (11g, 12g) and (11f, 12f) of the cuvette halves 11 and 12. The points of the cones (11g, 12g) and (11f, 12f) lie in the respective center points of the spheres 32a and 32b. The two cuvette halves 11 and 12 are placed one atop the other and, as shown in FIG. 3a, are placed in the adjusting tongs. After ending the application of pressure to locations 30a and 30b, the ends 31a and 31b are pulled together with the aid of spring 33 and cause the cuvette halves 11 and 12 to come in precisely the exact position by means of the conical recesses 32c and 32d.

Figure 3C:
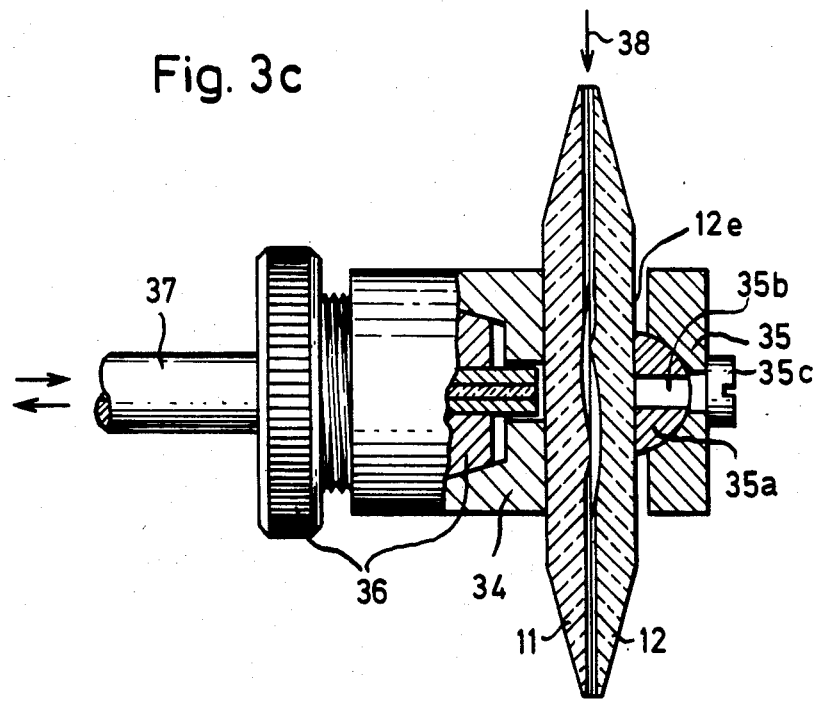
FIG. 3c shows the holder of FIG. 3b with a portion thereof broken away showing the interior thereof in section.
Figure 3B:
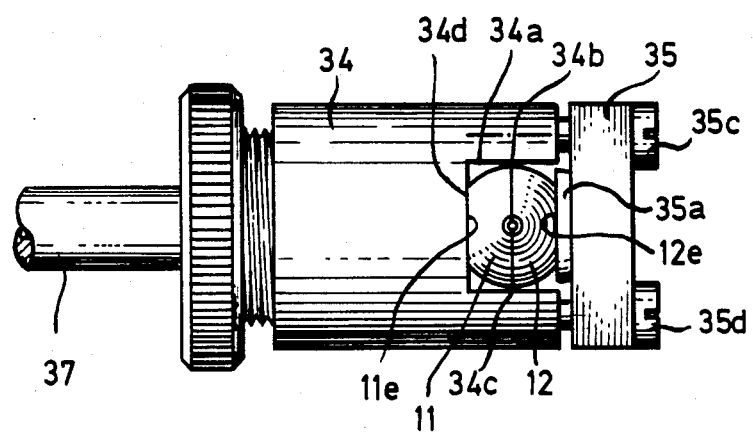
FIG. 3b is a cuvette holder for the two halves of the cuvette body.

The cuvette halves 11 and 12 then are placed in the cuvette holder while still being held by the adjusting tongs. FIGS. 3b and 3c show an embodiment of such a cuvette holder. The cuvette holder comprises a cylindrical base body 34 into which a recess 34a is milled and has a width so that the cuvette halves 11 and 12 just fit therein with a modicum of play (approximately 0.1 mm) at the locations 34b and 34c. The planar surface 11e of cuvette half 11 lies on the base 34d of the milled opening 34a. The part 35 is placed upon the opposite lying planar surface 12e of the other cuvette half 12. The part 35 includes a half-spherical insert 35a which is rotatably journalled therein. The part 35 is fastened to the base body 34 with screws 35c and 35d. The cuvette halves 11 and 12 are pressed together without any difficulty by means of the half-spherical insert 35a even when the part 35 becomes somewhat canted when the screws are tightened.

If both cuvette halves 11 and 12 are made of sapphire, then the half-spherical insert 35a should likewise be made of sapphire and the part 35 should be made of aluminum nitride or silicon nitride in order to obtain a good rotation of the parts with respect to each other. It is understood that a precise adjustment in the direction of flow 38 can be provided with mechanical means (not shown) when the cuvette halves 11 and 12 are placed in the base body 34 with the adjusting tongs thereby insuring that the measuring space 21 is placed at the correct position.

In the embodiment of a holder for a cuvette as shown in FIGS. 3b and 3c, a light conductor 37 directs the measuring light to and away and is fixed with the clamp 36 to the base body 34. In this instance, it is preferable that the half-spherically shaped insert 35a and the part 35 are provided with a bore 35b so that no disturbing reflection of the measuring light occurs on the surface 12e. It is understood that the cuvette can be utilized in through light and/or without light conductors.

If the reflected light is measured as shown in FIGS. 3b and 3c of the illustrated embodiment, then it is only necessary that the cuvette half 11 be made of optically transmittable material. In an advantageous embodiment of the invention, the cuvette half 12 is made from a material having a good heat conductance and which can be worked and polished such as beryllium oxide or aluminum nitride. A mirror layer made of platinum, iridium or rhodium can be vaporized or galvanically applied so that the surface, at least in the region 21, has approximately the same reflectivity as the optically transmittable material utilized for the cuvette half 11. In this embodiment, the half-spherical form 35a should also be made of beryllium oxide or aluminum nitride and the bore 35b should be omitted. The part 35 is in this case made of an especially fracture resistant ceramic such as silicon nitride or carbide metal.

Pursuant to a further embodiment of the invention, the part 35 can be provided with a good heat contact to a temperature regulating arrangement (not shown). However, in many applications the heat capacity of the cuvette half 12 and the parts 35a and 35 are adequate to maintain the temperature constant because of the small volume of the specimen. In this connection, the good heat contact to the relatively thin fluid layer at the surface 12a is most significant.

The embodiments of the cuvette described above are of primary importance for interferometric refractive index measurements. A suitable arrangement for this purpose is disclosed in applicants' U.S. patent application entitled "Interference Refractometer" having Ser. No. 722,111 and filed on Apr. 11, 1985.

An advantageous embodiment of the cuvette according to the invention for making absorption measurements is shown in FIG. 4. As a consequence of the very thin layer thickness, a one time or two time passage of the measuring rays is not sufficient for absorption measurements in order to obtain the desired sensitivity. Therefore, plane convex lens bodies 41 and 42 made of the same material as the cuvette halves 11 and 12 are cemented or preferably wringed (in optical contact) to the planar parallel outer surfaces 11e and 12e. The lens bodies 41 and 42 have respective spherical surfaces having layers of high reflectivity and defined residual transmittance (for example, 0.95/0.05). With respect to the latter, the radii of the spherical surfaces are so determined with respect to the spacings of the radial centers of the spherical surfaces that a confocal optical resonator results. In this way, an absorption spectrum is obtained having a band depth which is dependent upon the quality of the resonator for given extinction coefficients.

In the case of extremely high extinction coefficients, it can be useful to utilize multiple reflections at the surface of the specimen in lieu of multiple passes through the specimen. FIG. 5 shows a configuration of the cuvette according to the invention for this purpose. A trapezoidally formed prism body 51 is cemented or preferably wringed to the planar surface 11e of the cuvette half 11 and is made of the same material as that of the cuvette half 11. The two inclined trapezoidal surfaces 52 and 53 are mirrored spherical surfaces which define an optical resonator with a total reflection zone at the specimen surface in the middle of the resonator. In this case, an ATR-spectrum of the specimen is obtained.

In the manufacture of the cuvette, it is most important that the two cuvette halves 11 and 12 fit precisely atop one another so as to conjointly define an exact cuvette body 10 and that the convex recesses have the correct positions and center depths. This condition is realized in the manufacture of the cuvette in that two half cylinders are first produced and their planar surfaces are carefully worked so that these surfaces have an optical quality. These planar surfaces are then wringed to one another and, in this condition, the outer cylinder form and the cones at both ends are precisely produced. Thereafter, the cuvette halves are taken apart again and the planar outer surfaces 11e and 12e are produced. As a next step, the inlet and outlet channels 11b, 12b, 11d and 12d are milled into the cuvette halves with a diamond tool. For working in the convex recesses, each cuvette half with its corresponding planar surface 11e or 12e is blocked or wringed to a planar plate and two quadrilateral-shaped strips are wringed or cemented next to the longitudinal sides of the cuvette halves at a spacing which is not too great. The strips are somewhat higher and made of a material which is somewhat softer than that of the cuvette halves. If the cuvette halves are made of synthetic sapphire, for example, normal glass can be utilized for the strips. Now a lapping or polishing tool is utilized which has the desired radius of the spherical recess and a lapping or polishing means is used which removes material from the quadrilaterally-shaped glass strips but which does not remove any material from the cuvette half which is made of sapphire and is substantially harder. The corresponding lapping or polishing procedure then ends of necessity when the lapping or polishing tool touches the sapphire surface. An examining glass having the desired radius is now placed in the spherical ring surfaces worked out of the quadrilaterally-shaped strips. This touches the planar surface of the cuvette half made of sapphire in one point about which one can see an interference figure of concentric circles with suitable illumination. Now the cuvette half is aligned with respect to the quadrilaterally-shaped strips so that the contact point is precisely at the location at which the spherical recess in the cuvette body should be at its deepest location. After this alignment, a further removal common to both the cuvette half and the quadrilaterally-shaped strips results. Because of the minimal mid-depth of the spherical recess, only a polishing procedure can be undertaken for which the polishing means such as diamond paste or bore nitride can be utilized. The diameter of the spherical surface polished into the cuvette half in this manner is controlled from time to time with an examination glass. At the location where material is removed, no interference strips occur. The diameter determined in this manner can be converted into the corresponding mid-depth obtained.

For producing aspherical recess, only the last polishing procedure has to be changed. For this, the method and apparatus for producing aspherical and multifocal glasses can be utilized.

It is understood that the foregoing description is that of the preferred embodiments of the invention and that various changes and modifications may be made thereto without departing from the spirit and scope of the invention as defined in the appended claims.

What is claimed is:

1. A through-flow cuvette into which light is directed for making measurements on a fluid passing therethrough, the cuvette comprising:
    two cuvette body halves configured so as to permit assembly thereof to define the cuvette;
    at least one of said two body halves being made of an optically transparent material and having an outer surface region for receiving the light thereon;
    said cuvette body halves having a respective planar surfaces defining the interface between said body halves when said cuvette is assembled;
    each of said planar surfaces having an optical surface quality so as to cause said interface to be seal-tight with respect to the fluids passing therethrough;
    recess means formed in said planar surfaces to define a measuring space as well as inlet and outlet channels communicating with said space; and,
    said one body halve being a single solid piece consisting only of said optically transparent material and defining a window between said outer surface region and said measuring space for admitting the light into said measuring space.

2. A through-flow cuvette into which light is directed for making measurements on a fluid passing therethrough, the cuvette comprising:
    two cuvette body halves configured so as to permit assembly thereof to define the cuvette;
    at least one of said two body halves being made of an optically transparent material;
    said cuvette body halves having respective planar surfaces defining the interface between said body halves when said cuvette is assembled;
    recess means formed in said planar surfaces to define a measuring space into which the light is directed as well as inlet and outlet channels communicating with said space for conducting the fluid to and away from said measuring space; and,
    said recess means including two convex recesses formed in respective ones of said planar surfaces when said cuvette is assembled, said convex recesses being displaced with respect to each other in the direction of said channels so as to partially overlap and conjointly define said measuring space as having an approximately constant layer thickness.

3. The through-flow cuvette of claim 2, said body halves each having the same identical geometric dimensions and one of said body halves being rotated 180° when placed atop the other one of said body halves thereby causing the displacement of said convex recesses.

4. The through-flow cuvette of claim 2, each of said convex recesses being of spherical configuration.

5. The through-flow cuvette of claim 2, said body halves being configured so as to impart a spindle-like shape to said cuvette when the latter is assembled, said body halves having respective second planar surfaces parallel to each other and extending over a portion of the length of said cuvette in the longitudinal direction thereof, said body halves each having conical surface halves at respective ends thereof so as to cause the cuvette to have respective conical surfaces at its longitudinal ends when assembled, said inlet and outlet channels being formed in said first-mentioned planar surfaces so as to have respective outer ends at the longitudinal ends of said cuvette.

6. The through-flow cuvette of claim 1, at least one of said body halves being made of a material selected from the group consisting of: glass, quartz and sapphire.

7. The through-flow cuvette of claim 5, comprising planar-convex lenses mounted on corresponding ones of said second planar surfaces and having respective spherical surfaces; and, layer means formed on said spherical surfaces and having a high reflectivity with a defined residual transparency.

8. The through-flow cuvette of claim 7, said lenses being cemented to said corresponding ones of said surfaces.

9. The through-flow cuvette of claim 7, said lenses being in optical contact with said corresponding ones of said surfaces.

10. The through-flow cuvette of claim 5, comprising a trapezoidally formed prism mounted on one of said second planar surfaces, said prism having trapezoidal surfaces inclined toward each other; and, layer means formed on said trapezoidal surfaces and having a high reflectivity with a defined residual transparency.

11. The through-flow cuvette of claim 10, said prism being cemented to said one of said second planar surfaces.

12. The through-flow cuvette of claim 10, said prism being in optical contact with said one of said second planar surfaces.

13. The through-flow cuvette of claim 2, one of said body halves being made of a material selected from the group consisting of beryllium oxide or aluminum nitride; and, a layer formed at least on the convex recess of said last-mentioned body half, said layer being made of a material selected from the group consisting of platinum, iridium and rhodium.

14. The through-flow cuvette of claim 13, comprising temperature control means connected to said last-mentioned body half.

15. A through-flow cuvette into which light is directed for making measurements on a fluid passing therethrough, the cuvette comprising:

two elongated cuvette body halves configured so as to permit assembly thereof to define the cuvette;

said two body halves being solid pieces made of an optically transparent material;

said cuvette body halves having respective first planar surfaces defining the interface between said body halves when said cuvette is assembled;

each of said planar surfaces having an optical surface quality so as to cause said interface to be seal-tight with respect to the fluids passing therethrough;

recess means formed in said planar surfaces to define a measuring space as well as inlet and outlet channels communicating with said space;

said body halves having respective second planar surfaces parallel to each other and extending over a portion of the length of said cuvette in the longitudinal direction thereof; and, the first and second planar surfaces of said bodies being also parallel to each other so as to define respective windows for directing the light through said measuring space.

16. The through-flow cuvette of claim 15, said body halves being made of a material selected from the group consisting of: glass, quartz and sapphire.

17. The through-flow cuvette of claim 2, at least one of said body halves being made of a material selected from the group consisting: glass, quartz and sapphire.

* * * * *